United States Patent [19]

Baneyx et al.

[11] Patent Number: 5,552,301
[45] Date of Patent: Sep. 3, 1996

[54] PROCESS FOR ENCHANCING THE PRODUCTION OF HETEROLOGOUS PROTEIN IN BIOLOGICALLY ACTIVE CONFORMATION IN A TRANSFORMED E. COLI DNAK MUTANT HOST CELL

[75] Inventors: Francois Baneyx, Seattle, Wash.; Anthony A. Gatenby, Wilmington; Cathy E. Kalbach, Newark, both of Del.

[73] Assignee: E. I. Du Pont de Nemours and Company, Wilmington, Del.

[21] Appl. No.: 233,158

[22] Filed: Apr. 26, 1994

Related U.S. Application Data

[63] Continuation of Ser. No. 38,380, Mar. 29, 1993, abandoned.
[51] Int. Cl.$^6$ .................... C12N 15/00; C12N 15/73; C12P 21/00; C12P 21/02
[52] U.S. Cl. .................... 435/69.1; 435/69.4; 435/252.33
[58] Field of Search .................... 435/69.1, 172.1, 435/172.3, 69.4, 252.3–252.35, 320.1; 935/72, 73

[56] References Cited

U.S. PATENT DOCUMENTS 5,158,875 10/1992 Miller et al. .................... 435/69.1

FOREIGN PATENT DOCUMENTS

| | | |
|---|---|---|
| 0216747 | 4/1987 | European Pat. Off. . |
| 0225860 | 6/1987 | European Pat. Off. . |
| 85/03949 | 9/1985 | WIPO . |

OTHER PUBLICATIONS

Georgopoulos et al. Molec. Gen. Genet. 151: 35 (1977).
Goloubinoff et al, Nature 337: 44 (1989).
Somerville et al, Molec. Gen. Genet. 193: 214 (1984).
Wild et al, Proc. Natl. Acad. Sci. USA 89: 7139 (1992).
Easton et al, Gene 101, 291 (1991).
Obukowicz et al, *Applied and Environmental Microbiology*, 59(5), 1511 (1992).
Gamer et al, *Cell*, 69, 833 (1992).
Liberek et al, *Proc. Natl. Acad. Sci.*, 89, 3516 (1992).
Wild et al, *Genes & Development*, 6(7), 1165–1172 (1992).
Straus et al, *Genes & Development*, 4, 2202 (1990).
LaRossa et al, *Molecular Microbiology*, 5(3), 529 (1991).
Grossman et al, *Cell*, 38, 383 (1984).
Murby et al, *Biotechnology and Applied Biochemistry*, 14, 336 (1991).
Straus et al, *Genes and Development*, 3, 2003 (1989).
Yano et al, *J. of Bacteriology*, 172(4), 2124 (1990).
Wild et al, *Proc. Natl. Acad. Sci. USA*, 89, 7139–7143 (1992).
Somerville, et al, *Molecular & General Genetics*, 193(2), 214–219 (1984).
Goloubinoff, et al, *Nature*, 337, 44–47 (1989).
Georgopoulos, *Molecular & General Genetics*, 151(1), 35–39 (1977).

*Primary Examiner*—James Martinell

[57] ABSTRACT

Yield of biologically active foreign proteins from recombinent E. coli has been increased 2–4 fold by a novel use of the dnaK mutation. The presence of the full length dnaK mutant protein results in elevated levels of biologically active foreign proteins.

6 Claims, 1 Drawing Sheet

PROCESS FOR ENCHANCING THE PRODUCTION OF HETEROLOGOUS PROTEIN IN BIOLOGICALLY ACTIVE CONFORMATION IN A TRANSFORMED E. COLI DNAK MUTANT HOST CELL

This is a continuation of application Ser. No. 08/038,380, filed Mar. 29, 1993, now abandoned.

FIELD OF INVENTION

The invention relates to a method for enhancing the production of biologically active recombinant proteins in bacteria. More specifically, a method is disclosed wherein a heterologous protein is over expressed coincidentally with the manipulation of the central mechanism governing heat shock protein synthesis.

BACKGROUND OF THE INVENTION

Until now several commercially valuable proteins produced in recombinent bacteria were largely found to be recoverable primarily in a biologically inactive conformation. It has been necessary to refold those proteins into a biologically active conformation to obtain a profitable yield. By the use of recombinant DNA technology it is now possible to transfer DNA between different organisms for the purposes of expressing foreign proteins in biologically active conformation. Such transfer usually involves joining appropriate fragments of DNA to a vector molecule, which is then transformed into a recipient organism. Transformants are selected by a known marker on the vector, or by a genetic or biochemical screen to identify the cloned fragment. Vectors contain sequences that enable autonomous replication within the host cell, or allow integration into a chromosome of the host.

If the cloned DNA sequence encodes a protein, a series of events must occur to obtain synthesis of this foreign protein in a biologically active form in the host-cell. Promoter sequences must be present to allow transcription of the gene by RNA polymerase, and a ribosome binding site and initiation codon must be present in the transcribed mRNA for translation by ribosomes. These transcriptional and translational recognition sequences are usually optimized for effective binding by the host RNA polymerase and ribosomes, and by the judicious choice of vectors, it is often possible to obtain effective expression of many foreign genes in a host cell.

While many of the problems of efficient transcription and translation have been generally recognized and for the most part, overcome, the resulting synthesis of a foreign polypeptide frequently leads to low, or negligible, yields of biologically active protein. The over-expressed proteins often form inclusion bodies composed of aggregated inactive protein. The aggregated proteins must then be recovered and attempts made to refold the protein in vitro. Heterologous proteins may remain soluble in vivo, but may be subjected to proteolysis because of incorrect or incomplete folding in the unusual cellular environment (Kane et al., TIBTECH, 6, 95, (1988)). From such observations, it has become clear that factors that influence the folding of nascent polypeptide chains in vivo can have a considerable effect on the yield of foreign proteins produced from expression vectors in transformed cells.

The state of the art is illustrated by U.S. Pat. No. 5,158,875 to Miller et al. This patent to a method of producing insulin-like growth factor (IGF-1) recites a refolding step subsequent to harvesting IGF from the host cell. The step is recited as follows. "[R]efolding said Met-lys-IGF-I into its biologically active conformation." Clearly a commercially important limitation in the art is the inability to obtain commercial yield of some heterologous proteins in biologically active conformation.

A group of ancillary proteins, known as molecular chaperones, many of which are heat shock proteins (HSP), have been identified that have a profound influence on folding, recycling and synthesis of proteins. Prokaryotic molecular chaperones or HSP include such proteins as SecB, DnaK (hsp70 homologues in eukaryotic cells), DnaJ, GrpE, GroES (cpn10 homologues in eukaryotic cells) and GroEL (cpn60 or hsp60 in eukaryotic cells) (LaRossa et al., Mol. Micriobiol., 5 (3), 529, (1991)). The heat shock phenomenon, responsible for inducing the HSP or chaperones, was first defined as a response to a temperature up-shift. Subsequent work has Shown that exposure to a variety of stresses including phage infection, macrophage envelopment, as well as the presence of organic molecules and heavy metals can also trigger the heat shock response. Alternatively, the heat shock response may be artificially activated by the creation of various genetic mutants which constitutively express high levels of HSP, including molecular chaperones (LaRossa et al., Mol. Micriobiol., 5(3), 529, (1991)). The most extensively studied molecular chaperones are the GroES and GroEL proteins, and their eukaryotic homologues, collectively known as chaperonins.

The groE locus was first identified in studies of mutations that interfere with the assembly of the heads of bacteriophages lambda and T4 and the assembly of the tail of bacteriophage T5. The groE locus contains two genes, groEL and groES, both of which are essential for cell viability. The groEL and groES genes encode polypeptides with apparent relative molecular masses of 65,000 and 15,000, respectively, which are among the most abundant proteins in the cell. Both GroEL and GroES polypeptides are found in the cell as oligomeric structures. The GroEL protein is an ATPase, and the GroEL and GroES proteins form a complex with each other in the presence of MgATP and other nucleotides but not in their absence (Ellis et al., Biochem. Soc. Syrup., Kay et al. (Ed.) No. 55, 145, (1989)).

From in vitro studies, it is clear that a very wide range of unfolded or partially folded polypeptides interact with the GroEL protein, and that this interaction influences the subsequent folding reaction. When diluted from a denaturing solution, most proteins rapidly collapse to a non-native structure. Then, depending on the particular protein, its concentration, the temperature, and other factors, the non-native state will either progress to an active folded species, or will partition to a misfolded or aggregated state that is non-functional. If GroEL is present during dilution of unfolded proteins from the denaturing solution, the non-native proteins will bind to GroEL and form a stable binary complex. (Goloubinoff et al., Nature, 342, 884, (1989)). This has two possible consequences. For proteins that would normally continue to refold spontaneously, the folding reaction is arrested. In addition, proteins that would misfold and aggregate under these conditions are now bound to GroEL and remain in solution. Proteins bound to GroEL can be subsequently released by the addition of either ATP, or a combination of ATP and the chaperonin GroES. Under these conditions, proteins that would have folded anyway without the addition of GroEL, may continue to do so. However, proteins that would have aggregated are now directed towards the productive folding pathway. Survey-type experiments reveal that most E. coli proteins in a complex mixture, and many individual purified proteins, will interact with GroEL in this manner (Viitanen et al., *Protein Sci.*, 1, 363, (1992); Gatenby, *Plant Mol. Biol.*, 19, 677, (1992)).

In vivo studies also reveal that chaperones influence the successful folding of proteins into active molecules within cells. By using a cloned groE operon (encoding the genes for proteins GroES and GroEL) on a multicopy plasmid, it is possible to suppress a wide range of temperature sensitive missense mutations, indicating that successful folding of thermolabile enzymes can be restored by over-expression of the groES and groEL genes (Van Dyk et al., *Nature*, 342, 451, (1989)). By using combinations of compatible plasmids, where one plasmid encodes the groE operon, and the second plasmid encodes an overproduced foreign protein, it has been shown in several reports that the enhanced levels of molecular chaperones in the cell result in considerable improvements to the yield of functional recombinant protein (Goloubinoff et al., *Nature*, 337, 44, (1989); Berry-Lowe et al., *Plant Physiol.*, 99, 1597, (1992)).

There are, however, several inherent problems in the use of the dual plasmid system for enhanced production of foreign proteins in bacteria, especially for scale-up operations. Cloning of the groE operon on a multicopy plasmid leads to very high levels of synthesis of the GroES and GroEL proteins, with cells often producing 30–50% of their total cellular protein as GroEL. This results in a reduced biosynthetic capacity in the cell for other proteins, including the desired foreign protein, and overall yields may be reduced compared to the possible maximum. This high level production also influences groE plasmid stability, resulting in plasmid deletions that reduce expression of the groE genes. These deletions have been observed during long-term storage of strains, and during large scale culture of cells in the 10–200 l range (Kalbach et al., *Enzyme Microbiol. Technol.*, (in press) (1993)). In addition, it is apparent that the proper folding of proteins requires the concerted action of a number of different molecular chaperones, and is not confined to just GroES and GroEL (Langer et al., *Nature*, 356, 683, (1992)). Although the folding of some proteins is facilitated in vivo by groE over-expression, others do not respond to groE (Gatenby et al., *Trends in Biotechnology*, 8, 354, (1990)). The over-expression of a range of molecular chaperones may be required to assist the correct folding of proteins that do not respond to groE over-expression alone. This could be achieved by cloning all of the chaperone genes on compatible plasmids. However, this method would probably result again in strains harboring large unstable plasmids. A more preferred method might involve general activation of a broad range of native heat shock proteins in conjunction with the expression of the foreign protein.

It now appears that the regulation of general expression of heat shock proteins may be controlled by a few proteins, termed sigma factors. Sigma-32 is the most studied of these factors. Grossman et al. (*Cell*, 38, 383, (1984)) disclose that the htpR gene of *E. coli* encodes a positive regulator of the heat shock response. Over-expression of the htpR gene and subsequent purification of the protein product revealed a 32kDa protein termed, Sigma-32. Grossman et al. teach that the sigma-32 protein is responsible for transcription initiation at heat shock promoters. Grossman et al. additionally suggested renaming the htpR gene rpoH, and currently the two terms are used interchangeably.

By way of confirming the general function of the Sigma-32 factor, Yano et al. (*J. Bacteriol.*, 172, 2124, (1990)) teach a rpoH mutant that cannot grow at or above 34° C. since it produces an altered sigma-32 protein that is largely deficient in the transcription of the heat shock genes. Extragenic suppressor mutations endowed the rpoH mutant strain with the ability to grow at 40° C. and markedly enhanced the rate of sigma-32 synthesis and the induction of heat shock proteins.

Coupling of the regulation of the sigma-32 factor with the expression of foreign proteins is disclosed in the art. Debouck et al. (EP 216,747) teach a method of expressing a foreign polypeptide coding sequence in a htpR⁻ *E. coli* mutant, not stably expressed in htpR⁺ *E. coli* strains due to degradation by proteases under the control of the htpR⁺ gene. It is further disclosed that the htpR⁻ mutants do not code for wild-type sigma32 and thus are not able to undergo normal heat shock response. Similarly, Haley (WO 8503949) teaches the engineering of htpR⁻ mutants deficient in the production of the La protease for the expression of foreign polypeptides from *E. coli*. Abrahamsen et al. (EP 225,860) disclose a method for the expression and secretion of proteins in Gram negative bacteria by engineering into the host cell a DNA construct encoding a foreign protein where expression of the protein is dependent on the induction of the native htpR gene. The method of Abrahamsen relies on the generalized expression of heat shock proteins to give leakage of the periplasmic membrane of the transformed host, allowing for the secretion of the foreign protein into the growth medium.

Easton et al. (*Gene*, 101, 291, (1991)) disclose a method for the production of bovine insulin-like growth factor 2 (bIGF2) in the cytoplasm of *E. coli* containing a rpoH mutation. The bIGF2 was produced in inclusion bodies and constituted 20–25% of the total cellular protein. Similarly, Obukowicz et al. (*Appl. Environ. Microbiol.*, 58, 1511, (1992)) teach novel rpoH mutants for enhanced heterologous gene expression. Expression studies utilizing the recA or araBAD promoter and the phage T7 gene 10L ribosome-binding site showed that increased accumulation levels of a number of representative heterologous proteins were obtained in the rpoH mutants. Examples of heterologous proteins produced included human and bovine insulin-like growth factors 1 and 2, and bovine placental lactogen.

The methods recited above are useful for effecting the expression of recombinant proteins which are susceptible to sigma-32 dependent proteolysis or have a need to be secreted into the growth medium. With one exception, all the above cited art teaches that the down-regulation of the sigma-32 factor results in increased expression of foreign polypeptides. The most popular explanation for this phenomenon is that the rpoH⁻ mutants are deficient in the sigma-32 factor which results in impaired heat shock response. Higher expression of foreign proteins is expected in these mutants due to the absence of proteases resulting from the impaired heat shock response. Although the method of Abrahamsen (EP 225,860) teaches induction of the rpoH gene and the subsequent increase of heat shock proteins the primary motivation is to allow for the secretion of the protein by altering the permeability of the periplasmic membrane and no indication is given as to the levels of foreign protein expression by the host cell. It should be noted that inherent in the method of Abrahamsen is a fully functional wild-type DnaK protein. Additionally, it is known in the art that wild-type DnaK is functional in the facilitation of native protein secretion from *E. coli* (Wild et al., *Genes Dev.*, 6, 1165, (1992)).

Recent genetic evidence indicates that there are key regulator functions for another heat shock protein, DnaK, at the levels of synthesis, activity and degradation of sigma-32. DnaK, (a member of the Hsp70 protein family) is the 70kDa product of the dnaK heat shock gene and is thought to work in concert with other heat shock proteins to effect the refolding or synthesis of damaged cellular proteins (LaRossa et al., *Mol. Micriobiol.*, 5 (3), 529, (1991)). Mutations in dnaK, dnaJ and grpE have been shown to cause partial stabilization of sigma-32 and loss of repression of heat shock gene transcription normally found in wild-type cells after temperature downshift (Straus et al., *Genes Dev.*, 4, 2202, (1990) and Straus et al., *Genes Dev.*, 3, 2003, (1989)). The mechanism by which DnaK, DnaJ and GrpE regulate the activity and stability of sigma-32 is assumed to rely on their concerted activity as chaperones. This activity involves the ATP-dependant binding to substrates of DnaK and the stimulation of hydrolysis of DnaK-bound ATP by DnaJ and GrpE (Gamer et al., *Cell*, 69, 833, (1992)). It has been proposed that DnaK interacts with sigma-32 and dissociates it from RNA polymerase, thereby rendering it accessible to cellular proteases.

In contrast to the rpoH mutants, dnaK mutants have not been used heretofore for the expression of foreign polypeptides from recombinant bacteria. It would appear, in fact, that the presence of the DnaK protein may be necessary for the expression and secretion of some native and recombinant proteins. Wild et al. (*Genes Der.*, 6, 1165, (1992)) teach that translocation of alkaline phosphatase, was inhibited in dnaK mutant *E. coli* strains suggesting that export of this protein probably involves the DnaK protein. Murby et al. (*Biotechnol. Appl. Biochem.*, 14, 336, (1991)) disclose the coexpression of three recombinant proteins (human proinsulin, rat protein disulfide isomerase and the alpha.1.2.-chain of human T-cell receptor) as fusion proteins. Unexpectedly, the fusion proteins were found to be associated with DnaK and GroEL, indicating a function for these HSP in the expression of the foreign proteins. Similarly, Hellebust et al. (*J. Bacteriol.*, 172, 5030, (1990)) teach that protein A expressed by a recombinant *E. coli* is associated with the DnaK protein. Although it is clear that DnaK functions in the regulation of the sigma-32 factor, it is equally clear that it plays an important role in the facilitation of expression of various recombinant proteins.

The present invention provides a method which relies on a dnaK mutation for the purpose of enhancing the expression of biologically active heterologous proteins. The instant method is clearly distinguished from the art. The dnaK defective strain produces a defective DnaK protein. Sigma-32 is present in higher amounts in this mutant. The present invention takes advantage of this intracellular condition to enhance expression of biologically active heterologous proteins. Clearly the art has taught that foreign polypeptide expression is enhanced by lowering levels of sigma-32, ostensibly due to the lower protease levels achieved by the impaired heat shock response. The art also teaches that the wild-type DnaK protein is necessary and useful in the expression and secretion of heterologous proteins.

The instant invention provides a means to improve the yield of active foreign proteins produced in bacteria without having to subject the culture to a temperature shift, and without the necessity of a dual plasmid expression system. It is contemplated that the production yield of commercially valuable proteins, such as hormones, enzymes and other proteins can be improved if expression is performed by the instant method.

SUMMARY OF THE INVENTION

She present invention teaches a biologically pure culture of a transformed dnaK mutant *Escherichia coli* MF746 harboring an expression plasmid capable of producing heterologous protein in biologically active conformation.

The present invention also teaches a process for producing biologically active heterologous proteins in a transformed *Escherichia coli* dnaK mutant host cell, said process comprising:

a) expressing said heterologous protein in a biologically active conformation in said host cell; and b) harvesting said heterologous protein having a biologically active conformation from said host cell.

DETAILED DESCRIPTION OF THE INVENTION

Figure 1:
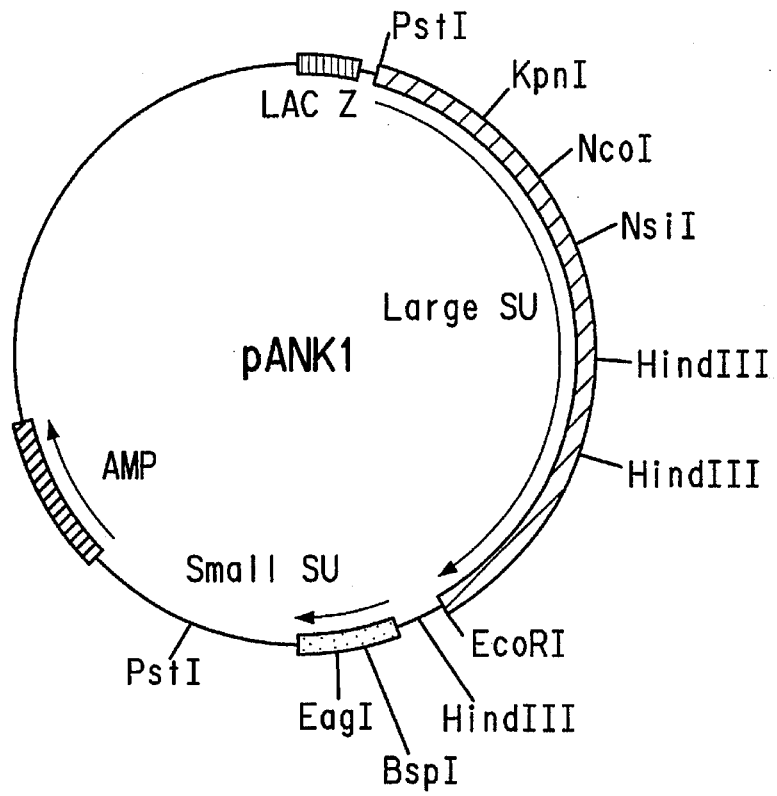
FIG. 1 is a plasmid map of the plasmid pANK1 encoding hexadecameric rubisco.

As used herein the following terms may be used for interpretation of the claims and specification.

The term "desired protein" refers to any protein considered a valuable product to be obtained from genetically engineered bacteria.

The terms "heterologous protein" and "foreign protein" refer to any protein not naturally found in the host cell. These terms are used interchangeably.

The term "biologically active protein" or "biologically active conformation" refers to a protein in a form capable of accomplishing the function it has in nature. Biologically active proteins useful in the present invention include, but are not limited to ribulose bisphosphate carboxylase, insulin-like growth factor-1, alfalfa glutamine synthetase, human medium-chain acyl-CoA dehydrogenase, amphibian superoxide dismutase, mammalian branched-chain alpha-ketoacid dehydrogenase and Brassica S-locus receptor kinase fusion protein.

The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

The term "fragment" or "DNA fragment" refers to a fraction of the DNA sequence of the particular region.

The terms "regulation" and "regulate" refer to the modulation of gene expression controlled by DNA sequence elements located primarily, but not exclusively upstream of (5' to) the transcription start of a gene. Regulation may result in an all or none response to a stimulation, or it may result in variations in the level of gene expression.

The term "construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" refers to the acquisition of new genes in a cell after the incorporation of nucleic acid.

The term, "operably linked" refers to the fusion of two fragments of DNA in a proper orientation and reading frame to be transcribed into functional RNA.

The term "expression" refers to the transcription and translation to gene product from a gene coding for the sequence of the gene product. In the expression, a DNA chain coding for the sequence of gene product is first transcribed to a complementary RNA, which is often a messenger RNA. The transcribed messenger RNA is translated into the gene product if the gene product is a protein.

The term "translation initiation signal" refers to a unit of three nucleotides (codon) in a nucleic acid that specifies the initiation of protein synthesis.

The term "plasmid" as used herein refers to an extra chromosomal element often carrying genes which are not part of the central metabolism of the cell, and usually in the form of circular double-stranded DNA molecules. Plasmids may be autonomously replicating or capable of integration into the host genome.

The term "restriction endonuclease" refers to an enzyme which binds and cuts within a specific nucleotide sequence within double-stranded DNA.

The term "heat shock protein" refers to any protein induced as a result of environmental stress, such as elevated temperature, or by the presence of an environmental insult, or by the expression of the sigma-32 subunit of RNA polymerase. Typical heat shock proteins include, but are not limited to those encoded by the genes groEL, groES, dnaK, dnaJ, grpE, lon, lysU, rpoD, htpG and clpB.

The term "DnaK" refers to a 70kDa heat shock protein involved in the regulation of the sigma-32 factor.

The term "dnaK" refers to the gene encoding the DnaK protein.

The term "dnaK mutant" refers to any host cell, prokaryotic or eukaryotic, that harbors a genetic mutation that results in an altered form of a DnaK protein and which consitutively produces high levels of heat shock proteins.

The term "sigma-32" refers to 32 kDa heat shock specific sigma subunit of a RNA polymerase which confers the ability to transcribe heat shock proteins to the polymerase.

The terms "peptide", "polypeptide" and "protein" are used interchangeably.

The term "molecular chaperone" is a functional definition refering to a group of unrelated proteins that mediate the correct folding of other polypeptides but are not themselves components of the final functional structures. Molecular chaperones can be involved in many cellular processes such as preventing premature folding or aggregation, mediating correct protein folding, facilitating secretion and membrane translocation.

The term "rubisco" refers to the enzyme D-Ribulose 1,5-bisphosphate carboxylase, E. C. 4.1.1.39.

As used herein, the designation "ATCC" refers to the American Tissue Culture Collection depository located in Rockville, Md. The "ATCC No." is the accession number to cultures on deposit at the ATCC.

The present invention discloses a process for enhanced production of foreign proteins in a biologically active form in bacteria. The process involves transforming a vector encoding a foreign gene into an *Escherichia coli* strain which contains a mutation such that the level of sigma-32 RNA polymerase subunit is increased, and the level of heat shock proteins in the cell is subsequently increased. Culturing the transformed mutant host at various temperatures and for various lengths of time leads to enhanced expression of the foreign protein as compared with wild-type transformants.

An important aspect of the present invention is the increase in the host cell level of heat shock proteins which takes place coincidentally with the expression of a foreign protein. Methods for increasing cellular levels of heat shock proteins might be divided into two categories comprising either direct induction of the heat shock response by factors external to the cell or alternatively, genetic manipulation of the host cell transcriptional or translational pathways. It is contemplated that either method is suitable for the purposes of the present invention.

Direct induction of the heat shock response may be effected by stressing the cell with any environmental insult or toxicant that will result in an alteration of normal cellular metabolism. Environmental insults may include, but are not limited to, chemicals, environmental pollutants, changes in temperature, changes in pH as well as agents producing oxidative damage, DNA damage, anaerobiosis, changes in nitrate availability or pathogenesis. Although typically the heat shock response has been associated with temperature changes many chemical substances have been shown to induce the response including $CdCl_2$, $H_2O_2$, ethanol, puromycin and nalidixic acid, (VanBogelen et al. *J. Bacteriol.*, 169(1), pp 26–32, (1987)) as well as benzene, Chlorpyrivos, 2,4-dichloraniline, dioctylphtalate, hexachlorobenzene, pentachlorophenol, trichloroethylene, and tetrapropylbenzosulfonate (Blom et al., *Appl. Environ. Microbiol.*, 58(1), pp 331–334, (1992)) to name a few. Although it is contemplated that inducing the heat shock response by environmental stress is possible for the instant method, it is not preferred as it is likely that environmental stress will also adversely affect cellular metabolism and therefore results in poor expression of foreign proteins.

Genetic manipulation of the heat shock response circumvents the necessity for exposing the cell to environmental stress, while at the same time altering levels of heat shock proteins in the cell. Typically these methods involve creating genetic mutants which either lack the ability to make the sigma-32 RNA polymerase subunit (e.g., rpoH mutants) resulting in lower levels of cellular heat shock proteins, or mutants which produce defective regulatory heat shock proteins (e.g., dnaK⁻ mutants) which are unable to inhibit either the synthesis or degradation of the sigma-32 subunit, resulting in high levels of cellular heat shock proteins. The present method insists on a host cell mutant comprising increased cellular level of heat shock proteins where dnaK mutants are preferred. Although the principle observations concerning the interaction of the dnaK gene and sigma-32 have been carried out in *E. coli*, dnaK and sigma-32 homologues have been isolated from variety of prokaryotic and eukaryotic species. It is contemplated that the present method would be operational in any species where up-regulation of sigma-32 results in an increase in cellular heat shock proteins. For the purposes of the present invention *E. coli* host cells harboring dnaK⁻ mutations are preferred.

dnaK mutants are known in the art. Wild et al. (P.N.A.S. USA, 89, 7139, (1992)) describe a set of 37 *E. coli.* dnaK mutants deficient in some aspect of the heat shock response. The present method relies on the dnaK⁻ mutant designated dnaK756 found in a host cell designated MF746 which is fully described by Georgopoulos, in *Molec. Gen. Genet.*, 151:35 (1977). This particular mutant has also been described as groPAB756, groPC756 and grpC756. dnaK756 was isolated in the presence of lambdoid bacteriophage and consequently will not allow lambda phage propagation. The block exerted by dnaK756 mutation on lambda phage growth has been shown to be at the level of phage DNA replication. It is thought that the dnaK756 mutation, harbored in the MF746 host is responsible for the production of an altered DnaK protein that inhibits the degradation of the sigma-32 subunit which results in elevated levels of heat shock proteins and molecular chaperones in the cell.

It will be appreciated by one of skill in the art of bacterial mutagenesis that, although DnaK756 is preferred by the instant method, any full length dnak mutation may be utilized. Methods for the selection of DnaK mutations are known and fall generally into two processes. In the first method (Georgopoulos et al., In: The *bacteriophage lambda* (A. D. Hershey, ed), 553, New York Cold Spring Harbor Laboratory, (1971)) a population of wild-type *E. coli* cells are mutagenized by exposure to nitrosoguanidine, allowed to grow in complete medium and then spread onto LB plates seeded with two different phages, $\lambda imm^\lambda cIh^\lambda$ and $\lambda imm^{434} cIh^{434}$. Large colonies that grow at 30° C. or 37° C. are isolated for characterization. The use of these two phages is to reduce growth of wild-type cells. One of skill in the art will appreciate that other combinations of phages could be used, and other mutagenesis protocols could work. Cells that grow on the selection plates are either mucoid, unable to adsorb either of the phages (and therefore appear phage resistant) or have a genetic block that prevents phage development. Colonies of the latter class will contain putative DnaK mutants. The nature of the mutation can be confirmed in two ways. Although a mutation in dnaK will disrupt phage DNA replication and growth, phages with mutations in the P gene ($\lambda \pi$) will grow on dnaK defective cells. Secondly, transducing phages that contain the host wt dnaK gene in their DNA will be able to grow on the mutant.

Another method (Itikawa et al., *J. Bacteriol.*, 138, 339, (1979)) to select mutations in dnaK relies on thymineless death at non-permissive temperatures. Cells are first mutagenized with nitrosoguanidine or another mutagen. Because dnaK mutations are often temperature sensitive for DNA synthesis at 43° C. wild-typ cells can be selected against by incubation at 43 ° C. in a medium without thymine. Surviving cells are enriched for those that do not undergo DNA synthesis and can then be recovered by growth on plates at a permissive temperature. The putative dnaK mutants can then be screened using the same spectrum of phage growth described above with $\lambda \pi$ and dnaK+ transducing phage and wild-type phage.

A variety of desired foreign proteins may be expressed by the instant method including proteins having industrial, research and pharmaceutical applications. Proteins most applicable to the present invention are those that have been demonstrated to rely on various heat shock proteins and molecular chaperones for correct structure. For example, Goloubinoff et al., (*Nature*, 342, 884, (1989)) have demonstrated that chemically denatured D-Ribulose 1,5-bisphosphate carboxylase, (rubisco) can be renatured in vitro by purified *E. coli* GroEL and GroES. Similar interactions with chaperones have been disclosed for pre-β-lactamase, citrate synthase, rhodanese and mouse dihydrofolate reductase (DHFR) (Viitanen et al., *Protein Science*, 1, 363, (1992)). Proteins of interest which may be expressed by the method and vector of this invention include, but are not limited to, enzymes such as carboxylases, decarboxylases, nitrogenases, collagenases, aminotransferases, reductases, dehydrogenases, synthetases, oxidases, as well as various other proteins such as hormones and antibody fragments. Preferred of the above mentioned enzymes and proteins are those known to be correctly folded in the presence of heat shock proteins and chaperones including *Anacystis nidulans* and *Rhodospirillum rubrum* ribulose bisphosphate carboxylase, *Klebsiella pneumoniae* nitrogenase, *Vibrio fischeri* LuxR regulatory protein, Human procollagenase, Barley glutamate 1-semialdehyde aminotransferase, Pea ferredoxin-NADP+ oxidoreductase, Mammalian branched-chain α-keto acid decarboxylase, Human growth hormone, Pig citrate synthase, *Bacillus stearothermophilus* lactate dehydrogenase, *Thermus thermophilus* isopropylmalate dehydrogenase and isocitrate dehydrogenase, *Bacillus stearothermophilus* glucose-6-phosphate dehydrogenase, Mitochondrial rhodanese, Yeast-glucosidase, Mouse monoclonal antibody $F_{ab}$ fragment, Recombinant immunotoxin, *Escherichia coli* glutamine synthetase, *Escherichia coli* tryptophanase, *Arthrobacter oxidans* 6-hydroxy-D-nicotine oxidase, Rat ornithine transcarbamoylase, and oat phytochrome. Most preferred are proteins drawn from the list consisting of dimeric and hexadecameric ribulose bisphosphate carboxylase, alfalfa glutamine synthetase, human medium-chain acyl-CoA dehydrogenase, amphibian superoxide dismutase, mammalian branched-chain alpha-ketoacid dehydrogenase and Brassica S-locus receptor kinase fusion protein.

The rubisco enzyme isolated from plants and photosynthetic bacteria and algae catalyzes the entry of $CO_2$ into the photosynthetic metabolism and provides acceptor molecules that consume the products of the light reactions of photosynthesis. Two types of rubisco with quite distinct quaternary structures are known. The simpler of the rubisco molecules originate from the purple nonsulfur photosynthetic bacteria *Rhodospirillum rubrum*. The oligomer is a dimer of identical large subunit polypeptides, each with a relative molecular mass of 50,500Da. The more common form of rubisco in plants and bacteria is the structurally more complex hexadecamer comprising eight large subunits each with a molecular mass of between 50,000Da and 50,500Da and eight small subunits each having a molecular mass of between 12,000Da and 18,000Da (Gatenby et al., TIBTECH., 8, 354, (1990)). It is notable that the method of the instant invention is capable of expressing both of these significantly different forms of the rubisco enzyme in biologically active form.

The present method also provides a vector capable of transforming a host cell comprising a heterologous DNA fragment encoding an expressible desired foreign protein. The vector contains sequences directing transcription and translation of the heterologous DNA fragment, a selectable marker, and sequences allowing autonomous replication or chromosomal integration. Suitable vectors comprise a region 5' of the heterologous DNA fragment which harbors transcriptional initiation controls, and a region 3' of the DNA fragment which controls transcriptional termination. It is most preferred when both control regions are derived from genes homologous to *E. coli* although it is to be understood that such control regions need not be derived from the genes native to the specific species chosen as a production host.

Initiation control regions, more commonly referred to as promoters, which are useful to drive expression of heterologous DNA fragments in *E. coli* are numerous and familiar to those skilled in the art. Virtually any promoter capable of driving the transcription of the gene encoding the desired protein is suitable for the present invention where the lac promoters are preferred.

Termination control regions may also be derived from various genes native to *E. coli* hosts, or optionally other bacterial or eukaryotic hosts or bacteriophages or viruses. Optionally, an *E. coli* termination site may be unnecessary, however, it is most preferred if included.

For intracellular production of the desired protein, DNA encoding said protein is linked operably through its initiation codon to the selected expression control region, such that expression results in the formation of the appropriate messenger RNA. Alternatively, if production of a fusion protein is desired, DNA encoding for the desired protein is linked at its 5' end to the 3' end of the gene encoding the fusion partner protein. Optionally the reverse orientation could be constructed where DNA encoding the fusion partner protein is linked at its 5' end to the 3' end of the DNA encoding the desired protein. Also, if desired, DNA coding for an enzyme or chemically cleavable linker is incorporated without reading frame disruption, between the DNA encoding the desired protein and the fusion partner-encoding DNA, so that expression yields a fusion protein from which the desired protein can be liberated by enzyme or chemical cleavage. An example of the fusion protein approach to protein production is provided by Contreras et al., *Bio Technology*, 9, 378,(1991).

The construction of a suitable vector for the expression of a desired protein in host of the instant invention may be accomplished by means well known to those skilled in the art. The source of the gene encoding the desired protein may either be chromosomal DNA or a previously constructed vector containing the gene.

The present method relies on two plasmids designated pANK1 (FIG. 1) and pRR2119 (FIG. 2). pANK1 comprises a DNA fragment encoding the large and small subunits of hexadecameric ribulose bisphosphate carboxylase-oxygenase (rubisco) from Synechococcus PCC6301 and is fully described in Newman and Gutteridge, *J. Biol. Chem.*, 265:15154 (1990). pRR2119 is a recombinant plasmid comprising a DNA fragment encoding the dimeric rubisco from *Rhodospirillum rubrum* and is fully described in Somerville, C. R. and Somerville, S. C., *Mol. Gen. Genet.*, 193:214 (1984).

The recombinant plasmid pANK1 was derived from pUC18 with the insertion of the gene encoding the hexadecameric form of the rubisco enzyme. Both the large and small subunit portions of the rubisco genes are under the control of the lacZ promoter (FIG. 1). As is well known in the art the lac promoter is normally repressed in *E. coli* hosts and may be induced by the addition of isopropyl-β-D-thiogalactoside (IPTG) which results in the expression of the rubisco gene. In addition, pANK1 contains a gene encoding ampicillin resistance, useful as a selectable marker.

Figure 2:
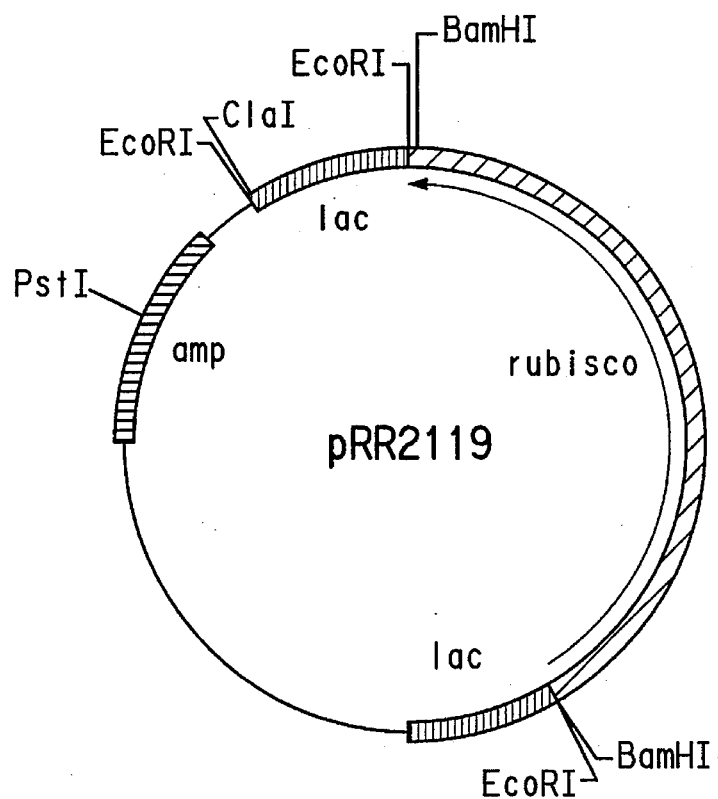
FIG. 2 is a plasmid map of the plasmid pRR2119 encoding dimeric rubisco.

The recombinant plasmid pRR2119 is 6.0 kb in size and was constructed from two other plasmids, pRR116 and pSG21 and contains the gene encoding dimeric rubisco under the transcriptional control of the *E. coli* lac promoter (FIG. 2). As with pANK1, pRR2119 contains a gene for ampicillin resistance and the rubisco gene is inducible with IPTG.

Host cells, either wild-type or containing the dnaK756 mutation may be transformed with the vectors of the instant invention by any means well known to those skilled in the art. Typically, cells were made competent by treatment with $CaCl_2$, transformed with the desired vector and the resulting transformants were screened by standard methods for ampicillin resistance on LB plates containing ampicillin. The *E. coli* host MF746 was transformed with either plasmid pANK1 or plasmid pRR2119 to produce the transformed hosts MF746 (pANK1) and MF746 (pRR2119), respectively. In similar fashion the *E. coli* host C600, wild-type for DnaK was also transformed with pANK1 or pRR2119 resulting in the transformants C600 (pANK1) and C600 (pRR2119).

For expression of the rubisco protein, individual colonies were cultured to a density of $A_{600}=0.3$ and induced with 1 mM isopropyl-β-D-thiogalactoside (IPTG). Samples were taken at hourly intervals and analyzed for the presence of rubisco.

In order to determine the levels of expressed rubisco protein induced cells were disrupted and analyzed for total protein and the presence of the rubisco enzyme. Cell disruption was accomplished using a French Press by standard methods and the cell extract was separated by centrifugation. Total protein was determined on the supernatant by the method of Biorad (Bio-Rad Laboratories, Richmond, Calif.) according to the protocol supplied by the manufacturer.

The presence of rubisco may be determined by a variety of methods including ELISA techniques (Metodiev, et al., *J, Exp. Bot.*, 43, 155 (1992)), or by spectrophotometric methods (Lan, et al., *Plant Physiol.*, 95: 604 (1991)). A preferred method involves the incorporation of radiolabeled $^{14}C$ as described in (Goloubinoff et al., *Nature*, 342, 884 (1989)). Briefly, 100 μl of cell extract supernatant was added to a solution containing 100 mM Bicine-NaOH pH 8.0, 20 mM $MgCl_2$, 1 mM dithiothreitol and 50 mM $NaH[^{14}C]O_3$ (0.22 mCi/mmol) and incubated at 25° C. for 10 minutes. 1 mM ribulose bisphosphate (RuBP) was then added and the mixture was incubated an additional 30 minutes when the reaction was terminated with 10% acetic acid. The addition of acetic acid drives off unincorporated $^{14}C$ and rubisco activity is measured as the formation of acid-stable $^{14}C$ in phosphoglyceric acid over 30 minutes at 25° C.

In the preferred embodiments of the invention foreign gene sequences cloned into a vector are transformed into an *E. coli* strain carrying the dnaK756 mutation. The vector contains sequences directing transcription and translation of the foreign gene, a selectable marker, and sequences allowing autonomous replication or chromosomal integration. Transformation and growth of overnight cultures is carried out at 30° C. to avoid selection of revertants at higher temperatures. The transformed host cells are cultured in an appropriate medium permitting growth of only the transformed organism. The cells are cultured at a constant temperature, within the range 30°–42° C. for an appropriate time after induction of expression of the foreign gene. When biologically active foreign protein accumulation has reached a plateau, cells are harvested, disrupted, and the foreign protein isolated.

Strains with the dnaK756 mutation contain an altered DnaK protein that fails to negatively regulate the heat shock response. Even at 30° C., dnaK756 cells exhibit enhanced levels of heat shock protein synthesis and accumulation, and the effect becomes more pronounced as the temperature of the culture medium is increased. During foreign protein production in dnaK756 at 30° C., enhanced yields of functional protein are obtained when compared to wild type dnaK strains. Yields are further enhanced as the temperature for cell growth is increased, and maximal accumulation of active foreign protein is obtained in the 37°–42° C. range.

It is to be noted that this invention is not dependent upon a biological explanation for the observation in the behavior of this expression system. Although the invention is not limited to any specific theory, we have a reasonable explanation for the observations made.

It is known that the dnaK756 strain synthesizes an altered form of the DnaK protein, which results in a heat sensitive phenotype, and the failure to support replication of bacteriophage DNA. The wild-type DnaK protein controls the level of expression of the heat shock or stress-regulated proteins in *E. coli*. In current models, this is achieved by the binding of DnaK to the sigma-32 subunit of RNA polymerase, which increases the sensitivity of this subunit to proteolysis, and thus reduces the level of this subunit in the cell. Expression of the heat shock genes requires transcription from specific promoters that are only recognized by RNA polymerase containing the sigma-32 subunit, so in the absence of this subunit expression is depressed. A property of the DnaK756 protein is that is does not bind effectively to the sigma-32 subunit, and so the subunit is not degraded as rapidly by proteases. The resulting higher levels of sigma-32 in the cell allow increased transcription from the sigma-32 controlled promoters, and the heat shock proteins, including the molecular chaperones, accumulate to higher than usual levels in the 30°–42° C. temperature range. The production of active foreign proteins expressed in the dnaK756 strain is enhanced compared to wild type dnaK strains.

The following examples are intended to illustrate the invention but are not meant to limit it in any way. Suitable methods of genetic engineering employed herein are described in Sambrook et al., Molecular Cloning: A Laboratory Manual—Volumes 1, 2, 3 (Cold Spring Harbor Laboratory: Cold Spring Harbor, N.Y., 1989), and in the instructions accompanying commercially available kits for genetic engineering. Bacterial cultures and plasmids to carry out the present invention are either commercially available or on deposit with the ATCC and, along with their sources, are identified in the text and examples which follow. Unless otherwise specified standard reagents and solutions used in the following examples were supplied by Sigma Chemical Co. (St. Louis, Mo.).

EXAMPLE 1

Enhanced production of the hexadecameric form of rubisco in *E. coli* strain MF746

*E. coli* strains MF746 and C600 were transformed with the rubisco expression plasmid pANK1, according to the procedure outlined below. Transformants were grown at 37° C. in liquid culture in LB media containing 0.2% glucose and 50 μg per ml ampicillin to $A_{600}$ 0.3, and induced with 1 mM IPTG. 15 ml samples were removed at 1 and 2 h following induction, and cells were disrupted and assayed as described above. Enzyme activity for both transformants is given in Table I and is expressed as nmol $CO_2$ incorporated into acid-stable material per min per mg protein.

Host bacteria

*E. coli* strain MF746 (thr-1, dnaK756, tonA21, lacY1, supE44, λ⁻) or *E. coli* strain C600 (thr-1, tonA21, lacY1, supE44, λ⁻) was used as a transformation recipients. *E. coli* strain MF746, and was obtained from Dr. Barbara J. Bachmann, *E. coli* Genetic Stock Center, Department of Biology 255 OML, Yale University, P.O. Box 6666, New Haven, Conn. 06511-7444. The Stock Center strain number is CGSC 5829. The strain has also been described as CG756 and GR756. The mutation of interest in the strain is dnaK756 (Georgopoulos, C. P., *Molec. Gen. Genet.* 151:35 (1977)). *E. coli* strain MF746 was derived from *E. coli* strain C600. *E. coli* strain C600 was used as a wild-type dnaK control. *E. coli* strain C600 was obtained from Stratagene, 11099 N. Torrey Pines Road, La Jolla, Calif. 92037.

Plasmids

The recombinant plasmid, pANK1, was obtained from Dr. S. Gutteridge, Central Research and Development, DuPont and encodes the genes for the large and small subunits of hexadecameric ribulose bisphosphate carboxylase-oxygenase (rubisco) from Synechococcus PCC6301.

*E. coli* transformation and growth

*E. coli* strain MF746 and *E. coli* strain C600 cells were made competent by $CaCl_2$ treatment, transformed with expression plasmids pANK1, and transformants selected on LB plates for ampicillin resistance containing 0.2% glucose and 50 μg/ml ampicillin at 30° C. Individual colonies were innoculated into liquid LB media containing 0.2% glucose and 50 μg/ml ampicillin, and cultured overnight with shaking at 30° C. The stationary phase cultures were diluted 1:50 into fresh media, and cultured with shaking at a constant temperature of 37° C. When the cell density had reached an $A_{600}$ of 0.3, a 15 ml aliquot was removed, cells were collected by centrifugation at 10000×g for 10 min, and the pelleted cells stored frozen. Following removal of the first aliquot, 1 mM isopropyl-β-D-thiogalactoside (IPTG) (BRL, Gaithersburg, Md.) was added to the remainder of the culture to induce expression of the plasmid-encoded foreign protein. Additional samples were removed at 1 hour intervals.

Cell disruption and protein analysis

Frozen cell pellets were thawed and resuspended in 3 ml 100 mM Bicine-NaOH pH 8.0, 20 mM $MgCl_2$, 1 mM dithiothreitol, 5 μg/ml deoxyribonuclease I, (Sigma Chemical Co. St. Louis, Mo.) followed by disruption by passage through a French pressure cell (SLM Instruments Inc.) at 20000 psi. The cell extract was centrifuged at 40000×g for 30 min and the supernatant retained. Total protein was determined on the supernatant by the method of Biorad (Bio-Rad Laboratories, Richmond, Calif.) according to the protocol supplied by the manufacturer.

Rubisco assays were carried out in a final volume of 300 μl containing 100 mM Bicine-NaOH pH 8.0, 20 mM $MgCl_2$, 1 mM dithiothreitol, 50 mM $NaH[^{14}C]O_3$ (0.22 mCi/mmol), 1 mM ribulose bisphosphate (RuBP) and 100 μl cell extract essentially as described in Goloubinoff et al., *Nature*, 342, 884 (1989). All components except RuBP were mixed in a volume of 288 μl and incubated at 25° C. for 10 min. Ribulose bisphosphate was obtained from the Sigma Chemical Co. (St. Louis, Mo.) and $NaH[^{14}C]O_3$ (0.22 mCi/mmol), was obtained from New England Nuclear Co. (Boston, Mass.).

The assay was initiated by the addition of 12 μl 25 mM RuBP and incubated for 30 min at 25° C. The reaction was stopped by the addition of 700 μl 10% acetic acid, and the contents of the reaction tubes were dried at 85° C. The dried residue was dissolved in 500 μl water, mixed with 10 ml Ready Safe scintillation cocktail, (Beckman Instruments) and incorporated radioactivity determined by liquid scintillation counting. Protein profiles in cell extracts were examined by electrophoresis on 6 or 10% polyacrylamide gels, in the presence or absence of sodium dodecyl sulfate, followed by staining of gels with Coomassie Brilliant Blue (Bio-Rad Laboratories, Richmond, Calif.).

TABLE I

Rubisco Activity in pANK1 Transformed *E. coli*

| Transformant | Enzyme Activity at Hourly Intervals Following IPTG Induction | |
|---|---|---|
| | 1 h | 2 h |
| C600 dnaK+ | 4.1 ± 1.9 | 6.9 ± 2.6 |
| MF746 dnaK756 | 11.7 ± 1.5 | 20.8 ± 1.2 |

As can be seen in Table I, expression of active hexadecameric rubisco is enhanced from 2 to 3 fold in the dnaK mutant strain as opposed to the wild-type.

*E. coli* strain MF746 was deposited on 18 Mar. 1993 with the ATCC under the terms of the Budapest treaty and is identified by the ATCC number 69267.

EXAMPLE 2

Enhanced production of the hexadecameric form of rubisco in *E. coli* strain MF746 at a range of temperatures

*E. coli* strains MF746 and C600 were transformed with the rubisco expression plasmid pANK1 as described above. Transformants were grown at 30°, 37° or 42° C. in liquid culture in LB media containing 0.2% glucose and 50 µg per ml ampicillin to $A_{600}$ 0.3. Rubisco expression was induced with 1 mM IPTG for 1 h, after which 15 ml samples were removed, and cells were disrupted and assayed as described above. Enzyme activity is for both transformants is given in Table II and is expressed as nmol $CO_2$ incorporated into acid-stable material per min per mg protein.

Host bacteria

*E. coli* strain MF746 (thr-1, dnaK756, tonA21, lacY1, supE44, λ-) or *E. coli* strain C600 (thr-1, tonA21, lacY1, supE44, λ-) was used as a transformation recipients.

Plasmids

The recombinant plasmid, pANK1, was obtained from Dr. S. Gutteridge, Central Research and Development, DuPont and encodes the genes for the large and small subunits of hexadecameric ribulose bisphosphate carboxylase-oxygenase (rubisco) from Synechococcus PCC6301. Plasmid pANK1 is described in Newman, J. and Gutteridge, S., *J. Biol. Chem.* 265: 15154 (1990).

*E. coli* transformation and growth

Cells of *E. coli* strain MF746 and *E. coli* strain C600 were made competent by $CaCl_2$ treatment, transformed with expression plasmids pANK1 and transformants selected on LB plates for ampicillin resistance containing 0.2% glucose and 50 µg/ml ampicillin at 30° C. Individual colonies were inoculated into liquid LB media containing 0.2% glucose and 50 µg/ml ampicillin, and cultured overnight with shaking at 30° C. The stationary phase cultures were diluted 1:50 into fresh media, and cultured with shaking at a constant temperature selected at 30°, 37°, and 42° C. in separate culture flasks. When the cell density had reached an $A_{600}$ of 0.3, a 15 ml aliquot was removed, cells were collected by centrifugation at 10000×g for 10 min, and the pelleted cells stored frozen. Following removal of the first aliquot, 1 mM isopropyl-β-D-thiogalactoside (IPTG) (BRL, Gaithersburg, Md.) was added to the remainder of the culture to induce expression of the plasmid-encoded foreign protein. Additional samples were removed at 1 hour post-induction.

Cell disruption and protein analysis

Frozen cell pellets were thawed and resuspended in 3 ml 100 mM Bicine-NaOH pH 8.0, 20 mM $MgCl_2$, 1 mM dithiothreitol, 5 µg/ml deoxyribonuclease I. Cell disruption, total protein determination and Rubisco assay were carried out as described in Example 1.

TABLE II

Rubisco Activity in pANK1 Transformed *E. coli*

| Transformant | Enzyme Activity After 1 h IPTG Induction at Different Temperatures | | |
|---|---|---|---|
| | 30° C. | 37° C. | 42° C. |
| C600 dnaK+ | 2.7 ± 1.9 | 7.6 ± 3.2 | 4.1 ± 1.6 |
| MF746 dnaK756 | 10.4 ± 1.8 | 22.2 ± 0.6 | 15.1 ± 4.5 |

As can been seen in Table II expression of active hexadecameric rubisco is enhanced from 3 to 4 fold in the dnaK mutant strain as opposed to the wild-type.

*E. coli* strain MF746 containing Rubisco expression plasmid pANK1 was deposited on 18 Mar. 1993 with the ATCC under the terms of the Budapest treaty and is identified by the ATCC number 69268.

EXAMPLE 3

Enhanced production of the dimeric form of rubisco in *E. coli* strain MF746

*E. coli* strains MF746 and C600 were transformed with the dimeric rubisco expression plasmid pRR2119. Transformants were grown at 37° C. in liquid culture in LB media containing 0.2% glucose and 50 µg per ml ampicillin to $A_{600}$ 0.3. A 15 ml sample was removed, 1 mM IPTG added for induction, and a second 15 ml sample removed after 1 h post-induction. Cells were disrupted and assayed as described in above. Enzyme activity for all transformant is given in Table III and is expressed as nmol $CO_2$ incorporated into acid-stable material per min per mg protein.

Host bacteria

*E. coli* strain MF746 (thr-1, dnaK756, tonA21, lacY1, supE44, λ-) or *E. coli* strain C600 (thr-1, tonA21, lacY1, supE44, λ-) was used as a transformation recipients.

Plasmids

The recombinant plasmid pRR2119 was obtained from Dr. C. R. Somerville, (DOE Plant Research Laboratory, Michigan State University, East Lansing, Mich. 48824) and encodes the gene for dimeric rubisco from *Rhodospirillum rubrum*. Plasmid pRR2119 is described in Somerville, C. R. and Somerville, S. C., Mol. Gen. Genet. 193:214 (1984).

E. coli transformation and growth

*E. coli* strain MF746 (thr-1, dnaK756, tonA21, lacY1, supE44, λ-) or C600 (thr-1, tonA21, lacY1, supE44, λ-) was used as a transformation recipients. Using techniques well known to those skilled in the art, cells were made competent by $CaCl_2$ treatment, transformed with expression plasmid pRR2119, and transformants selected on LB plates for ampicillin resistance containing 0.2% glucose and 50 µg/ml ampicillin at 30° C. Individual colonies were inoculated into liquid LB media containing 0.2% glucose and 50 µg/ml ampicillin, and cultured overnight with shaking at 30° C. The stationary phase cultures were diluted 1:50 into fresh media, and cultured with shaking at a constant temperature selected at 37° C. When the cell density had reached an $A_{600}$ of 0.3, a 15 ml aliquot was removed, cells were collected by centrifugation at 10000×g for 10 min, and the pelleted cells stored frozen. Following removal of the first aliquot, 1 mM isopropyl-β-D-thiogalactoside (IPTG) (BRL, Gaithersburg, Md.) was added to the remainder of the culture to induce expression of the plasmid-encoded foreign protein. Additional samples were removed at 1 hour post-induction.

Cell disruption and protein analysis

Frozen cell pellets were thawed and resuspended in 3 ml 100 mM Bicine-NaOH pH 8.0, 20 mM $MgCl_2$, 1 mM dithiothreitol, 5 μg/ml deoxyribonuclease I, (Sigma Chemical Co., St. Louis, Mo.). Cell disruption total protein determination and Rubisco assay were carried out as described in Example 1.

TABLE III

| Rubisco Activity in pRR2119 Transformed E. coli | | |
|---|---|---|
| | Enzyme Activity Before and After 1 Hour Induction with IPTG | |
| Transformant | 0 h | 1 h |
| C600 dnaK+ | 7.1 ± 0.7 | 18.6 ± 3.9 |
| MF746 dnaK756 | 18.8 ± 2.5 | 29.2 ± 2.3 |

As can be seen by the data in Table III expression of dimeric rubisco is enhanced 1.5 to 2.5 fold in the dnak756 mutants as opposed to the wild-type host.

E. coli strain MF746 containing Rubisco expression plasmid pRR2119 was deposited on 18 Mar. 1993 with the ATCC under the terms of the Budapest treaty and is identified by the ATCC number 69266.

What is claimed is:

1. A process for using a transformed *Escherichia coli* dnaK mutant host cell to produce heterologous protein in biologically active conformation, said process comprising:

a) expressing in said dnaK mutant host cell said heterologous protein having a biologically active conformation and being either a full length mutant protein or a partially inactivated but functional mutant protein; and b) harvesting said heterologous protein having a biologically active conformation from said host cell.

2. A process according to claim 1 wherein said heterologous protein is drawn from the group consisting of dimeric D-ribulose 1,5-bisphosphate carboxylase, hexadecameric D-ribulose 1,5-bisphosphate carboxylase, insulin-like growth factor (IGF-1), alfalfa glutamine synthetase, human medium-chain acyl-CoA dehydrogenase, amphibian superoxide dismutase, mammalian branched-chain alpha-ketoacid dehydrogenase, and Brassica S-locus receptor kinase fusion protein.

3. A process according to claim 1 wherein the dnaK mutation results in a full length mutant protein.

4. The process of claim 1 wherein the transformed dnaK mutant host cell is selected from the group of materials designated ATCC 69266 and ATCC 69268.

5. A biologically pure culture of a transformed dnaK mutant *Escherichia coli* MF746 designated ATCC 69268 which harbors the pRR2119 plasmid and produces heterologous protein in biologically active conformation.

6. A biologically pure culture of a transformed dnaK mutant *Escherichia coli* MF746 designated ATCC 69266 which harbor the pANK1 plasmid and produces heterologous protein in biologically active conformation.

* * * * *